United States Patent [19]

Bernstein

[11] 4,311,791

[45] Jan. 19, 1982

[54] AUTOMATED KINETIC DETERMINATION OF LACTATE DEHYDROGENASE ISOENZYMES IN SERUM

[76] Inventor: Larry H. Bernstein, 2800 Gaslight La., East, Mobile, Ala. 36609

[21] Appl. No.: 158,121

[22] Filed: Jun. 10, 1980

Related U.S. Application Data

[63] Continuation of Ser. No. 912,745, Jun. 5, 1978, abandoned.

[51] Int. Cl.³ ............................................. C12Q 1/32
[52] U.S. Cl. ..................................... 435/26; 435/184
[58] Field of Search ................... 435/26, 805, 810, 184

[56] References Cited

U.S. PATENT DOCUMENTS 3,862,010  1/1975  Rush et al. ............................. 435/26
4,003,795  1/1977  Lamprecht ............................. 435/26

OTHER PUBLICATIONS

Wilkinson, *Diagnostic Enzymology*, Edward Arnold Publishers, Ltd., London, (1976), pp. 46–54.
Bergmeyer, et al., *Methods of Enzymatic Analysis*, vol. 2, Academic Press Inc., N.Y. (1974), pp. 574–578, 603–612.
Cabaud, et al. "Colorimetric Measurement of Lactic Dehydrogenase Activity of Body Fluids," *Am. J. Clin. Path.*, vol. 30, No. 3, (1958), pp. 234–236.
Howell, et al. "Lactate-to-Pyrauate or Pyrauate-to-Lactate Assay for Lactate Dehydrogenase; A Re-examination," *Clin. Chem.*, vol. 25, No. 2, (1979), pp. 269–272.
Plagemann, et al, "The Electrophoreticlly Distinct Forms of Mammalian Lactic Dehydrogenase," *J. Biol. Chem.*, vol. 235, No. 8, (1960), pp. 2288–2293.

*Primary Examiner*—Thomas Wiseman

[57] ABSTRACT

A diagnostic method is disclosed, based on the automated kinetic determination of LDH and MDH isoenzymes in serum, which utilizes the comparison of two rates of LDH and MDH activity at different concentrations of substrate. A step is eliminated from the procedure previously proposed, significantly improving the method. The method is based on the principle that the pure and hybrid forms of LDH and MDH isoenzymes differ in their affinities for and are inhibited to different extends by their substrate.

2 Claims, No Drawings

AUTOMATED KINETIC DETERMINATION OF LACTATE DEHYDROGENASE ISOENZYMES IN SERUM

This case is a continuation of U.S. Ser. No. 912,745, filed June 5, 1978, abandoned.

INTRODUCTION

Malate dehydrogenase (MDH) exists as mitochondrial (mMDH) and cytoplasmic (cMDH) isozymes. These isozymes differ in their physical and chemical properties. Consequently, their separation may be carried out using differential centrifugation, ion-exchange chromatography or electrophoresis prior to assay of their fractional MDH activities. However, these methods are laborious and may not be suitable for applications requiring many measurements at frequent time intervals.

It has been known for some time that the mitochondrial and cytoplasmic MDH isozymes are differentially inhibited by high concentrations of oxaloacetate (OAA). This inhibition is similar to the inhibition exhibited by lactate dehydrogenase (LDH) in the presence of high concentrations of pyruvate. The inhibition of LDH has been shown to be directly related to the formation of an abortive ternary complex which is not an intermediate in the catalytic pathway. Similarly, MDH forms an abortive complex among the enzyme, NAD+ and OAA which inhibits the catalytic reaction.

This application discloses a kinetic method for automated determination of Lactate Dehydrogenase Isoenzymes in Serum.

GENERAL STATEMENT OF INVENTION

A steady-state kinetic method has been revised for measuring lactate dehydrogenase isoenzyme activities, which relates the inhibition of heart-type isoenzyme activity to the overall isoenzyme composition of the enzyme subunits. The method depends on the pH-dependent formation of an inhibitory ternary complex by the heart-type isoenzyme with NAD+ and pyruvate (if the reaction is measured by NADH oxidation). A preincubation step in the previous method is eliminated. The isoenzymes are measured by measuring the reduction of pyruvate in two different concentrations, which favor either the total or fractional activity, depending on the concentrations of pyruvate and the percentage of heart-type subunits. The method has been adapted to a centrifugal analyzer, which has speeded automated isoenzyme determinations, with an accuracy comparable to that for electrophoretic methods.

These studies also determine the levels of malate dehydrogenase (MDH) isoenzymes in cardiac muscle by a steady state kinetic method, which depends on the differential inhibition of these isoenzyme forms by high concentrations of oxaloacetate. This inhibition is similar to that exhibited by lactate dehydrogenase in the presence of high concentrations of pyruvate. The results obtained by this method are comparable in resolution to those obtained by CM-Sephadex fractionation and by differential centrifugation for the analyses of m-MDH and c-MDH in tissues. The use of standard curves of percent inhibition of MDH activity plotted against the m/(m+c) MDH ratio (percent m-type) is introduced for studies of comparative mitochondrial function in heart muscle of different species or in different tissues of the same species.

STATEMENT OF PRIOR ART

Most procedures for determining the lactate dehydrogenase (LD, EC 1.1.1.27) isoenzyme activities are based on their different physical and kinetic properties: thermal stability, solubility in organic solvents, stability against urea denaturation, and Michaelis constants.

Methods involving kinetic measurements of the activities of the two isoenzymes are usually accurate, rapid, and inexpensive, and adaptable to automated instruments. In addition, because these activities in the body fluids vary with time, it is useful to be able to measure them sequentially by kinetic methods. One such method is promising but does not lend itself to automation because it requires two assays, before and after a preincubation step.

I have revised the conditions for such a determination so that the preincubation step is eliminated and the procedure can be adapted to automated kinetic instruments such as the centrifugal analyzer.

MATERIALS USED IN THE METHOD ACCORDING TO THE INVENTION:

Sodium pyruvate (Grade A, Calbiochem., San Diego, Cal. 92037).

NADH (Standard Grade, P-L Biochemicals, Inc., Milwaukee, Wis. 53205).

Serum and tissue samples from patients were obtained from the Tampa Veterans Administration Hospital.

METHODS CARRIED OUT

Preparation of tissue. Human tissue extracts were prepared by sonic disruption (at 4° 1 C. for 1 min.) of 1 g (wet weight) of tissue in 9 ml of potassium phosphate buffer (0.1 mol/liter, pH 7.0). The homogenates were centrifuged at 4° C. at $5 \times 10^4$ g for 10 min.; and the superiors were promptly examined for LD activity and stored at $-80°$ C.

Assay for total LD activity. The measurements were at 340 nm and 25° C. in a Model 240 (Gilford Instrument, Oberlin, Ohio 44074) digital kinetic spectrophotometer when manual determinations were needed to supply data for calibration curves with purified enzymes or with tissue extracts, and for serum assays in the preliminary stages of developing the method. Sera were assayed at 25° C. in a centrifugal analyzer (GEM-SAEC; Electronucleonics, Inc., Fairfield, N.J. 07006) after the optimum conditions were known to be suitable for manual determinations. For automated determinations 500 ul of pyruvate reaction mixture and 50 ul of serum (an 11-fold dilution of the serum) were required. Conditions for measuring total LD activity were: 0.34 mmol of pyruvate and 0.13 mmcl of NADH per liter of the phosphate buffer. The molar absorptivity $6.22 \times 10^3$ liter $mol^{-1}$ $cm^{-1}$ for NADH was used in calculating enzyme activity in IUB units.

Determination of isoenzymes by electrophoresis. LD isoenzymes in serum were separated on "Poly E Film" (Pfizer Diagnostics, Clifton, N.J. 07012), stained with "Poly E-Strate" (Pfizer), and scanned in a Model R-111 densitometer (Beckman Instruments, Inc., Fullerton, Calif. 92634) at 575 nm. The ratios of the H/M subunits were calculated from the known percentages of H-type and M-type LD activities in the hybrid and pure LD isoenzymes, the sum of all isoenzyme activities being considered 100%.

Kinetic determination of isoenzymes. LD's are inhibited by their substrate, the H-type LD being inhibited by pyruvate to a greater extent than the M-type LD. This inhibition, related to the formation of an abortive ternary complex, was the basis of the method that has been used to distinguish the heart enzyme from the muscle enzyme after preincubation.

Conditions for inhibiting the human LD activity without any preincubation were: 5 mmol of pyruvate and 0.13 mmol of NADH per liter of 100 1 mmol/liter potassium phosphate buffer, pH 7.0. At the conditions of the assay there was a slight inhibition of the M-type LD and more than 50% inhibition of the H-type LD, which permitted the best resolution of LD mixtures of their isoenzyme subunit composition.

RESULTS

Assay conditions. Studies of the pH dependence of the inhibition of chicken heart LD at an initial substrate concentration of 3.4 mmol/liter pyruvate (control rate, 0.1 absorbance unit change per minute at 0.34 mmol/liter pyruvate) indicated the pH for maximum inhibition of LD activity to be pH 7, although pH 6.5 was also suitable for the inhibition. At pH 8 and above, no inhibition was seen. However, when mixtures of crystalline chicken heart and rabbit muscle LD were assayed for isoenzyme activity, the crystalline rabbit muscle LD reacted at 114% of the maximum velocity at 3.4 mmol/liter pyruvate because of its higher $K_m$ for pyruvate and the greater amount of pyruvate necessary to inhibit the LD activity. The rabbit muscle was saturated and was also inhibited by 2% at a concentration of 10 mmol/liter pyruvate, whereas the chichen heart LD was inhibited 75%. Similarly, 5 mmol/liter pyruvate and pH 7.0 were the most suitable conditions for the human LD from liver and from heart, as indicated by the large difference between the inhibition of the LD activity from these cell extracts, and because of the low inhibition of the muscle type LD (Table 1).

TABLE 1

INHIBITION OF LD ACTIVITIES IN EXTRACTS OF HUMAN HEART AND LIVER BY HIGH CONCENTRATIONS OF PYRUVATE AT DIFFERENT CONDITIONS

| Pyruvate mmol/liter | pH | Percent inhibition a.b.c Heart | Liver |
|---|---|---|---|
| 10 | 6 | 91 | 65 |
| 5 | | 90 | 53 |
| 10 | 7 | 79 | 50 |
| 5 | | 69 | 20 |
| 10 | 8 | 50 | −14 |
| 5 | | 40 | −19 |

[a]Assay conditions were: 100 mmol/liter potassium phosphate buffer pH 7.0, containing 0.34 mmol/liter pyruvate for measurement of total LD activity.
[b]5 and 10 mmol/liter pyruvate were used to inhibit LD activity.
[c]Negative sign indicates increased rate of LD activity at higher concentrations of pyruvate.

Subunit composition in LD mixtures. The human heart extract was mixed with liver cell extracts in the following proportions: 100, 75, 50, 25 and 0 ml/dl. Assays of these mixtures resulted in a decreased percentage inhibition of LD activity that could be defined by the equation[1] $y = 50.2 - 0.066x - 0.004x^2$; $r^2 = 0.993$ (F=134), where y=percent inhibition of LD activity and x=percent muscle LD activity. To test the ability to measure the amounts of pure M and H subunits, I assayed mixtures of pure crystalline beef heart H₄ and rabbit muscle M₄ LD for their percent inhibition by pyruvate. I found a decreased percentage inhibition of LD activity with decreasing amount of H₄ LD activity, which could be defined by the equation[1] $y = 74.0 + 0.062x - 0.005x^2$; $r^2 = 0.984$ (F=61), where y=percent inhibition of LD activity and x=percent muscle LD activity.

The two curves for percent inhibition of LD activity obtained on using human tissue extracts and using purified mammalian crystalline H₄ and M₄ LD isoenzymes, were compared and the relationship between them could be defined by the equation $y = 18.59 + 0.902x$; $r^2 = 0.992$ (F=361), where y=% inhibition of human LD activity, and x=% inhibition of purified LD.

LD isoenzymes of human tissues. Table 2 compares the inhibition profiles for human tissue LD by the revised method with those previously reported. Except in the case of brain, the inhibition profiles are very similar by the two methods. However, the revised method may readily be automated for use with the centrifugal analyzer.

TABLE 2

PERCENT INHIBITION OF LD FROM HUMAN TISSUES, AS MEASURED BY TWO METHODS[a]

| | Percent inhibition[b] | |
|---|---|---|
| Tissue | Preincubation method | Present method |
| Heart | 61.1 ± 8.3 | 60.8 ± 10.8 |
| Liver | 18.3 ± 10.0 | 17.6 ± 11.8 |
| Kidney | 53.0 ± 15.1 | 53.1 ± 5.0 |
| Brain | 59.0 ± 6.6 | 50.6 ± 8.4 |
| Spleen | 41.3 ± 8.5 | 43.5 ± 9.0 |
| Muscle | 17.3 ± 12.2 | 16.1 ± 11.8 |

[a]Determinations were carried out on samples from at least seven sources.
[b]Mean ± 2 SD (range of LD activity).

Correlation of LD by electrophoresis. When the method was compared with electrophoretic determination of H/M subunit composition of serum LD activity in patients, a linear relationship was defined by the equation $y = 0.886x + 7.6$, where y=percent of heart LD kinetically determined and x=percent of heart LD electrophoretically determined. The correlation coefficient ($r^2 = 0.851$) was significant [F(63)=165].

DISCUSSION

Several reports indicate that the activity of the two LD subunit types of human serum and tissues may be estimated by kinetic methods by using the inhibition of LD activity by high pyruvate concentrations. However, a method is needed that can be carried out by steady-state kinetics, with use of a variety of instruments found in most clinical laboratories, and that could be automated for use with centrifugal analyzers.

This procedure does not substantially affect the results for H/M isoenzyme content of tissues as compared with those previously reported. In addition, a good correlation between H/M LD isoenzyme composition as determined by kinetic and electrophoretic methods indicates that the method gives results that agree with those for a comparison method already in use. Although the kinetic method measures the subunit composition as a function of the percent inhibition of subunits, electrophoresis requires a series of manipulations that introduce a multiplicative error into the determination. Finally, the faster determination of serum isoenzymes in critically ill patients would permit frequent serial isoenzyme determinations, to determine the severity of and the progress of recovery from acute myocardial infraction.

REFERENCE TO PRIOR ART

Bernstein, L. H., Everse, J., Shioura, N., and Russell, P. J., Detection of cardiac damage using a steady state assay for lactate dehydrogenase isoenzymes in serum. *J. Mol. Cell. Cardiol.* 6, 297 (1974).

Bernstein, L. H. and Everse, J., Determination of the isoenzyme levels of lactate dehydrogenase. In *Methods in Enzymology*, 41, W. A. Wood, Ed., Academic Press, New York, New York, 1975, pp. 47–50.

The embodiments of the invention in which an exclusive property or privilege is claimed are defined as follows:

1. A method of measuring isoenzymes selected from the group consisting of lactate dehydrogenase and malate dehydrogenase in body fluids, said method being adapted for use in automated instruments and operable without a preincubation, said method comprising,
   (a) contacting a first portion of a body fluid sample suspected of containing the isoenzymes with a reagent composition containing an oxidized substrate selected from the group consisting of pyruvate and oxaloacetate and nicotinamide-adenine dinucleotide under conditions suitable for enzymatic activity and at a controlled pH of 7 or less wherein the oxidized substrate and nicotinamide-adenine dinucleotide are present in non-rate limiting amounts,
   (b) measuring the enzymatic activity of said first portion to obtain a first measurement,
   (c) contacting a second portion of said body fluid sample with a reagent composition containing said oxidized substrate and nicotinamide-adenine dinucleotide under conditions suitable for enzymatic activity and at a controlled pH of approximately 7, wherein said oxidized substrate is present in an amount at least 10 times the amount of step (a) and the isoenzyme concentration is approximately the same as step (a),
   (d) measuring the enzymatic activity of said second portion to obtain a second measurement,
   (e) comparing said first measurement to said second measurement to obtain the difference in activities whereby the amount of isoenzymes is measured as the amount of inhibited isoenzymes activity.

2. The method of claim 1 wherein the oxidized substrate in said second reaction solution is ten to twenty times the concentration of said oxidized substrate in said first reaction solution.

* * * * *